US008716687B2

(12) United States Patent
Goldstein et al.

(10) Patent No.: US 8,716,687 B2
(45) Date of Patent: May 6, 2014

(54) METHOD AND APPARATUS FOR SHIELDING MEDICAL PERSONNEL FROM RADIATION

(75) Inventors: James Goldstein, Bloomfield Hills, MI (US); Mark A Fox, Leesburg, IN (US)

(73) Assignee: Eco Cath-Lab Systems, Inc., Bloomfield Hills, MI (US)

( * ) Notice: Subject to any disclaimer, the term of this patent is extended or adjusted under 35 U.S.C. 154(b) by 611 days.

(21) Appl. No.: 12/935,722

(22) PCT Filed: Mar. 31, 2009

(86) PCT No.: PCT/US2009/039038
§ 371 (c)(1),
(2), (4) Date: Mar. 21, 2011

(87) PCT Pub. No.: WO2009/124094
PCT Pub. Date: Oct. 8, 2009

(65) Prior Publication Data
US 2011/0248193 A1   Oct. 13, 2011

Related U.S. Application Data

(60) Provisional application No. 61/040,801, filed on Mar. 31, 2008.

(51) Int. Cl.
*G21F 3/02* (2006.01)
*G21F 3/00* (2006.01)

(52) U.S. Cl.
USPC ................ 250/519.1; 250/515.1; 128/849

(58) Field of Classification Search
USPC ............... 250/505.1, 515.1, 516.1, 519.1; 128/846, 849, 853–855; 378/203; 252/478
See application file for complete search history.

(56) References Cited

U.S. PATENT DOCUMENTS

| 4,938,233 | A  | * | 7/1990  | Orrison, Jr. ............... 128/849 |
| 6,448,571 | B1 | * | 9/2002  | Goldstein ................ 250/515.1 |
| 6,653,648 | B2 | * | 11/2003 | Goldstein ................ 250/515.1 |
| 6,674,087 | B2 | * | 1/2004  | Cadwalader et al. ....... 250/515.1 |
| 7,091,508 | B2 | * | 8/2006  | Goldstein ................ 250/515.1 |
| 7,303,334 | B2 | * | 12/2007 | Cadwalader et al. ......... 378/203 |
| 7,391,042 | B2 | * | 6/2008  | Goldstein ................ 250/515.1 |
| 7,638,784 | B2 | * | 12/2009 | Fox et al. ................. 250/515.1 |
| 7,767,990 | B2 | * | 8/2010  | Cadwalader et al. ....... 250/519.1 |
| 7,829,873 | B2 | * | 11/2010 | Fox et al. ................. 250/515.1 |
| 2004/0161076 | A1 | * | 8/2004  | Goldstein ................... 378/160 |
| 2005/0213713 | A1 | * | 9/2005  | Cadwalader et al. ......... 378/203 |
| 2006/0284123 | A1 | * | 12/2006 | Goldstein ................ 250/515.1 |
| 2008/0093568 | A1 | * | 4/2008  | Fox et al. ................. 250/515.1 |
| 2008/0164425 | A1 | * | 7/2008  | Cadwalader et al. ....... 250/492.1 |
| 2012/0132217 | A1 | * | 5/2012  | Rees ........................... 128/849 |

\* cited by examiner

*Primary Examiner* — Bernard E Souw
(74) *Attorney, Agent, or Firm* — Dentons US LLP

(57) ABSTRACT

Systems and methods for shielding medical personnel from radiation are provided. A radiation-shielding barrier is positioned between the medical personnel and the radiation source. The radiation-shielding barrier includes an opening such that a portion of the table extends through the opening in the barrier. Medical personnel are protected from secondary radiation transmitted through the patient via a special layering technique of a first, flexible sterile drape, a flexible radiation-resistive drape, and a second flexible sterile drape. The system includes an upper shield and a lower shield of independent movement and a linking mechanism between the two, while maintaining the radiation seal. The system also includes a mechanism for maintaining the radiation barrier between the upper shield and the patient aperture hoop, preventing a radiation gap from forming between the flexible portions of the system (e.g. flexible drapes, curtains, etc.) and the non-flexible portions of the system (e.g. upper shield, lower shield, radiopaque transparent window, etc.).

15 Claims, 19 Drawing Sheets

METHOD AND APPARATUS FOR SHIELDING MEDICAL PERSONNEL FROM RADIATION

CROSS-REFERENCE TO RELATED APPLICATIONS

This application is a U.S. National Stage of PCT/US09/039,038, filed 31 Mar. 2009, which claims the priority benefit of and incorporates by reference U.S. Provisional Patent Application No. 61/040,801 filed Mar. 31, 2008, both of which are incorporated herein by reference in entirety.

FIELD OF THE INVENTION

The present invention relates generally to radiation protection systems. More specifically, the present invention relates to methods for shielding persons (e.g., medical personnel) from radiation emitted by a radiation source during a radiologic procedure performed on a patient.

BACKGROUND OF THE INVENTION

Radiographic equipment (e.g., x-ray equipment) is used when performing a wide variety of medical procedures. For example, radiographic equipment is used by cardiologists when positioning heart catheters in patients. Many procedures such as these require medical personnel to be in direct contact with the patient, thereby preventing the personnel from being in a separate room and potentially exposing the medical personnel to radiation. For this reason, radiation shields are used during radiographic procedures to reduce radiation exposure. Radiation shields typically are constructed of materials such as lead that significantly reduce the transmission of radiation. For example, some shields include lead plates mounted on stands that may be adjusted to position the plates between the medical personnel and sources of radiation. Despite the use of these shields, medical personnel are still exposed to radiation. Exposure comes from many radiation sources other than the primary source. For example, a significant secondary radiation source is radiation transmitted through the patient, even through the patient's extremities, to the medical personnel.

Cumulative long-term radiation exposure may cause significant adverse affects to medical personnel. Medical personnel performing radiographic procedures typically spend many hours over their careers performing such procedures. Medical personnel typically wear protective clothing, including a full lead apron, a thyroid collar and leaded glasses, to reduce radiation exposure while performing the procedures. However, wearing heavy lead protective clothing may have long-term adverse effects, including disabling spinal disorders. Although there are many prior art radiation protection systems for protecting and shielding medical personnel from radiation exposure, these systems often require medical personnel to wear protective clothing. Therefore, there is a need for systems that reduce or eliminate the need for wearing protective clothing to reduce or eliminate the effects of wearing the protective clothing.

SUMMARY OF THE INVENTION

In one aspect, the present invention includes methods and apparatus for shielding medical personnel from radiation emitted by a radiation source during a radiologic procedure performed on a patient. The patient is supported by a table. A radiation-shielding barrier is positioned between the medical personnel and the radiation source. The radiation-shielding barrier is also positioned adjacent the table. The radiation-shielding barrier includes an opening such that a portion of the table extends through the opening in the barrier. In some embodiments, this opening is a patient aperture hoop of adjustable size, through which a portion of the table may extend and through which at least a portion of a patient may extend.

Medical personnel are protected from secondary radiation transmitted through the patient via the following special layering technique. As a first layer, at least a portion of the patient is covered with a first, flexible sterile drape. As a second layer, at least a portion of the first flexible sterile drape is covered with a flexible radiation-resistive drape. As a third layer, at least a portion of the flexible radiation-resistive drape is covered with a second flexible sterile drape.

The system includes an upper shield and a lower shield of independent movement. One aspect of the present invention includes a linking mechanism between the upper and lower shield. The linking mechanism allows independent movement of the upper shield relative to the lower shield (and vice-versa) within a limited range of motion, while maintaining the radiation seal. Stated differently, the linking mechanism allows for the relatively independent repositioning of the upper and lower shields without exposing the medical personnel to radiation from the radiation source (i.e. no radiation gap between the upper and lower shield during repositioning).

The system also includes a mechanism for maintaining the radiation barrier between the upper shield and the patient aperture hoop. The mechanism (e.g. a unidirectional chain) maintains the radiation seal and prevents a radiation gap from forming between the flexible portions of the system (e.g. flexible drapes, curtains, etc.) and the non-flexible portions of the system (e.g. upper shield, lower shield, radiopaque transparent window, etc.).

The foregoing and other objects are intended to be illustrative of the invention and are not meant in a limiting sense. Many possible embodiments of the invention may be made and will be readily evident upon a study of the following specification and accompanying drawings comprising a part thereof. Various features and subcombinations of invention may be employed without reference to other features and subcombinations. Other objects and advantages of this invention will become apparent from the following description taken in connection with the accompanying drawings, wherein is set forth by way of illustration and example, an embodiment of this invention and various features thereof.

BRIEF DESCRIPTION OF THE DRAWINGS

A preferred embodiment of the invention, illustrative of the best mode in which the applicant has contemplated applying the principles, is set forth in the following description and is shown in the drawings and is particularly and distinctly pointed out and set forth in the appended claims.

FIG. 13a is a top view of the linking mechanism; FIG. 13b is a partial sectional view of the linking mechanism.

Corresponding reference characters indicate corresponding parts throughout the several views of the drawings.

DETAILED DESCRIPTION OF THE PRESENTLY PREFERRED EMBODIMENTS

A detailed embodiment of the present inventions is disclosed herein; however, it is to be understood that the disclosed embodiment is merely exemplary of the principles of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 1:
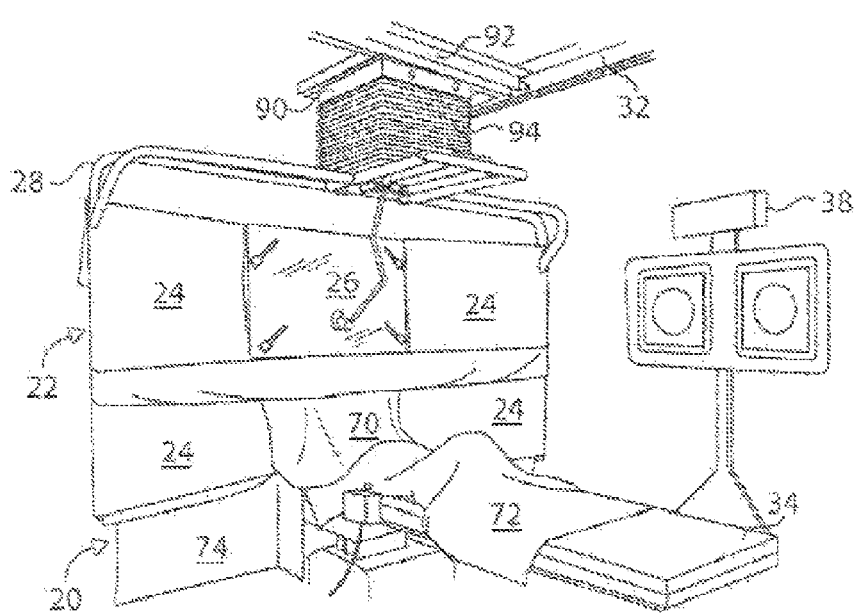
FIG. 1 is a perspective of a radiation protection system according to principles of the present invention.

Referring now to the drawings and in particular FIG. 1, a radiation protection system of one embodiment of the present invention is designated in its entirety by the reference numeral 20. The system 20 comprises an upper radiation-shielding barrier, generally designated by 22, including flexible panels 24 and a visually transparent window 26, both of which have low radiation transmissivity, mounted on a frame 28. The system 20 also includes a lower shield 74 moveably attached to the upper shield 22 via a linking mechanism (not shown in FIG. 1). The radiation-shielding barrier 22 is positioned adjacent and above a table 34. During a radiologic procedure, a patient is supported by the table 34. The radiation-shielding barrier 22 is also positioned between a radiation source 36 (FIG. 2 and FIG. 5) and medical personnel performing a radiologic procedure on the patient. The table 34, radiation source 36, and radiographic monitoring equipment 38 are conventional and will not be described in further detail.

As further illustrated in FIG. 1, a flexible, radiation-resistive, interface 70 is fastened to the barrier 22 to cover an opening between the barrier 22 and the table 34 and patient. A flexible, radiation-resistive, drape 72, such as a lead blanket, is positioned over the patient. The interface 70 and flexible radiation-resistive drape 72 reduce radiation from being transmitted to the medical personnel through the patient, especially the lower extremities of the patient. Although the interface 70 and radiation-resistive drape 72 may be made of other materials without departing from the scope of the present invention, in one embodiment they include lead sheets wrapped in sterile vinyl covers. The interface 70 and drape 72 may be attached to the radiation-shielding barrier 22 and each other using any suitable fasteners such as hook and loop fasteners, screws, snaps, adhesives, or Velcro fasteners. Thus, the system 20 provides a complete radiation barrier between the radiation source 36 and medical personnel, as well as between the patient and the medical personnel. The system 20 also blocks all other substantial secondary sources of radiation. In fact, it is believed that the system 20 can block more than 99% of all radiation that would otherwise reach the medical personnel, thereby eliminating the need for heavy protective clothing.

Figure 2:
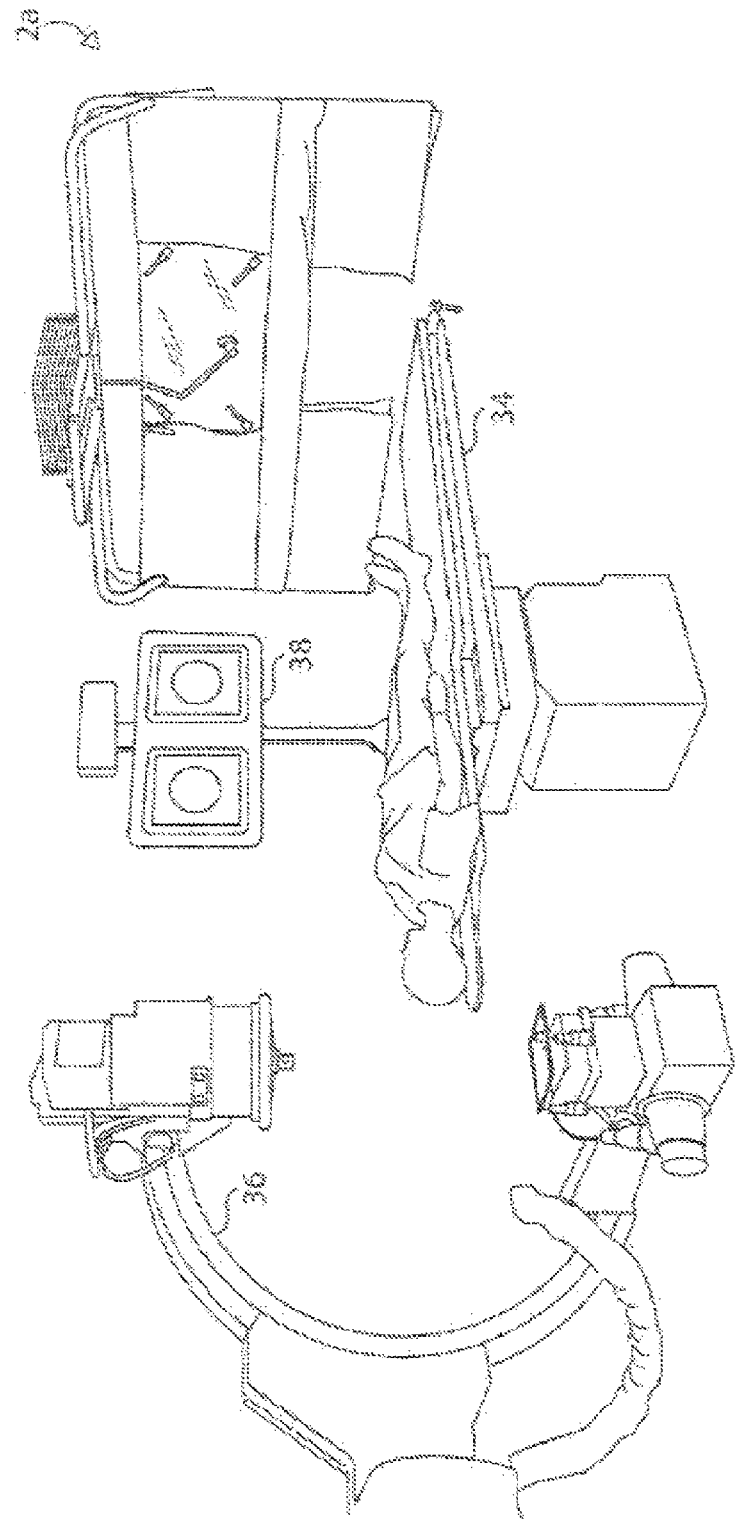
FIG. 2 is an alternate perspective of the radiation protection system shown in FIG. 1 with the radiation-shielding barrier stored away from other equipment.

Referring to FIG. 2, the barrier 22 may be attached to the table 34 so that it moves concurrent with the table 34 or it may be unattached to the table 34 so that the table 34 and barrier 22 can move independently. For example, the barrier 22 may be moved to a position remote from the table 34 and source 36 as shown in FIG. 2 to permit the radiographic equipment 38 to be used without the barrier 22 or to permit the patient to be positioned onto and removed from the table.

Figure 3:
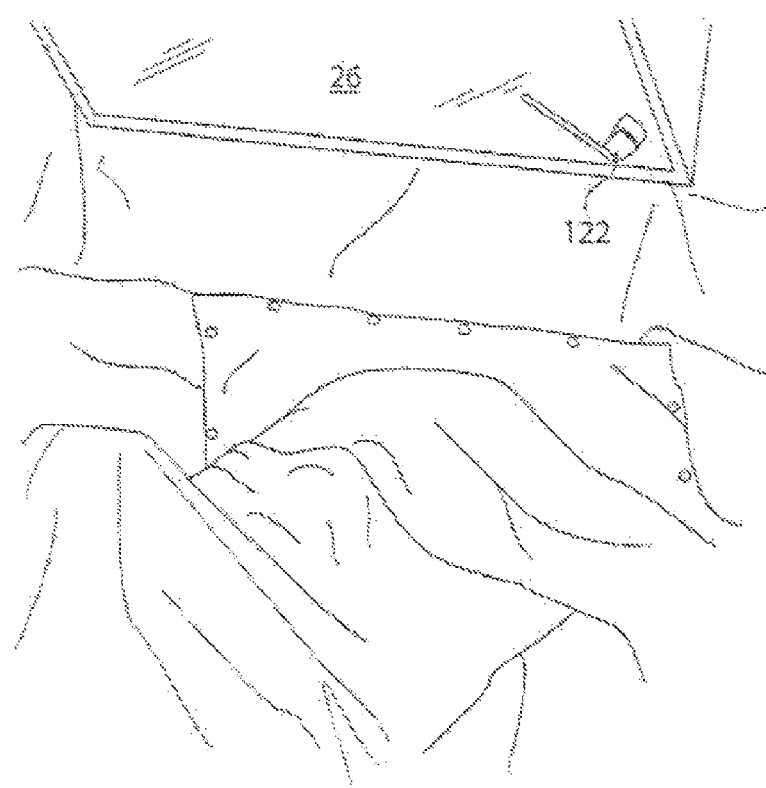
FIG. 3 is a detail of the system shown in FIG. 1.

FIG. 3 illustrates an embodiment of the fasteners used to connect the interface 70 and/or drapes to the barrier 22. The barrier 22 includes an opening such that the table 34 or the table 34 and a patient can extend through the opening in the barrier 22. As shown in FIG. 3, the interface 70 covers the opening in the barrier 22 and also a portion of the table 34 and patient. A radiation-resistive drape 72 also covers a portion of the patient, especially the lower extremities.

In some embodiments, medical personnel are protected from secondary radiation transmitted through the patient via the following special layering technique. As a first layer, at least a portion of the patient is covered with a first, flexible sterile drape. As a second layer, at least a portion of the first flexible sterile drape is covered with a flexible radiation-resistive drape. As a third layer, at least a portion of the flexible radiation-resistive drape is covered with a second flexible sterile drape. The three layers may be executed simultaneously or one after the other. In other embodiments, the layering technique is achieved by inserting a reusable radiation-resistant flexible sheet into a pocket between two flexible sterile drapes that are connected to each other along at least one edge. In other embodiments, a single flexible sterile drape is folded over on top of itself to form the first and second layers.

Figure 4:
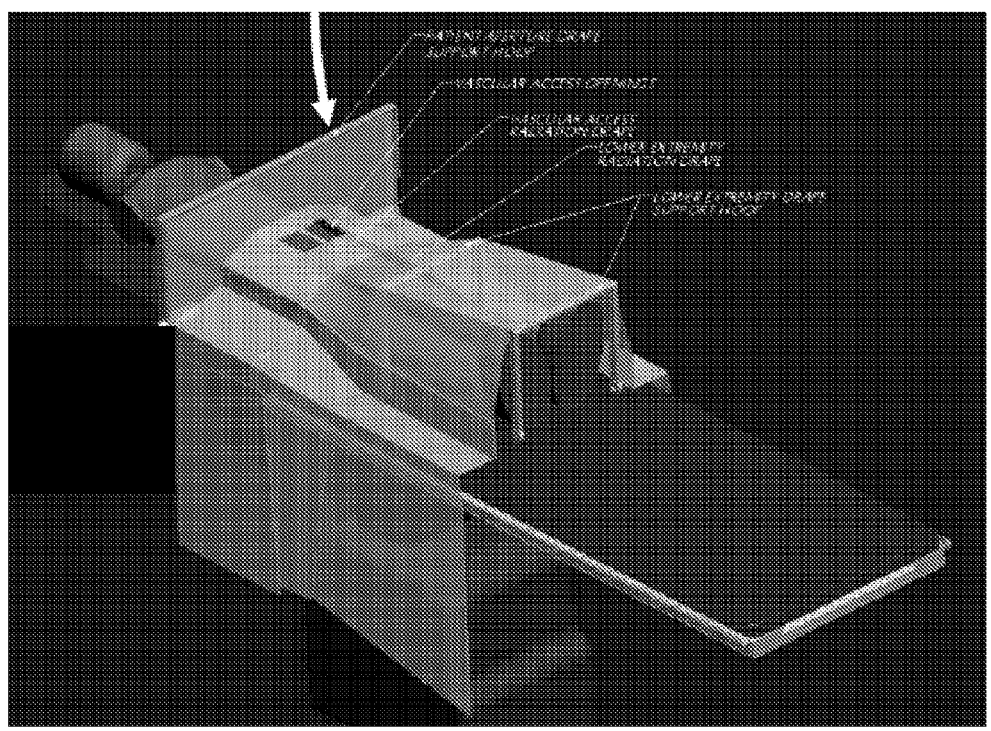
FIG. 4 is a perspective of an embodiment according to principles of the present invention with the radiation-shielding barrier removed.

Referring to FIG. 4, an embodiment of the present invention is shown, with the radiation-shielding barrier 22 removed for clarity. In FIG. 4, only the opening in the barrier 22 is shown. The interface 70 covers the opening in the barrier 22 and a portion of the patient. A radiation-resistive drape 72 covers an additional portion of the patient, especially the lower extremities. In FIG. 4, openings are shown in one embodiment of the radiation-resistive drape 72 for allowing access to the patient while minimizing radiation exposure to medical personnel. The openings in the radiation-resistive drape 72 may be covered by inserts having smaller apertures to further reduce radiation exposure. In embodiments where the layering technique is employed, each layer includes one or more apertures. In some embodiments, the apertures of each of the three layers are all aligned with one another.

Figure 5:
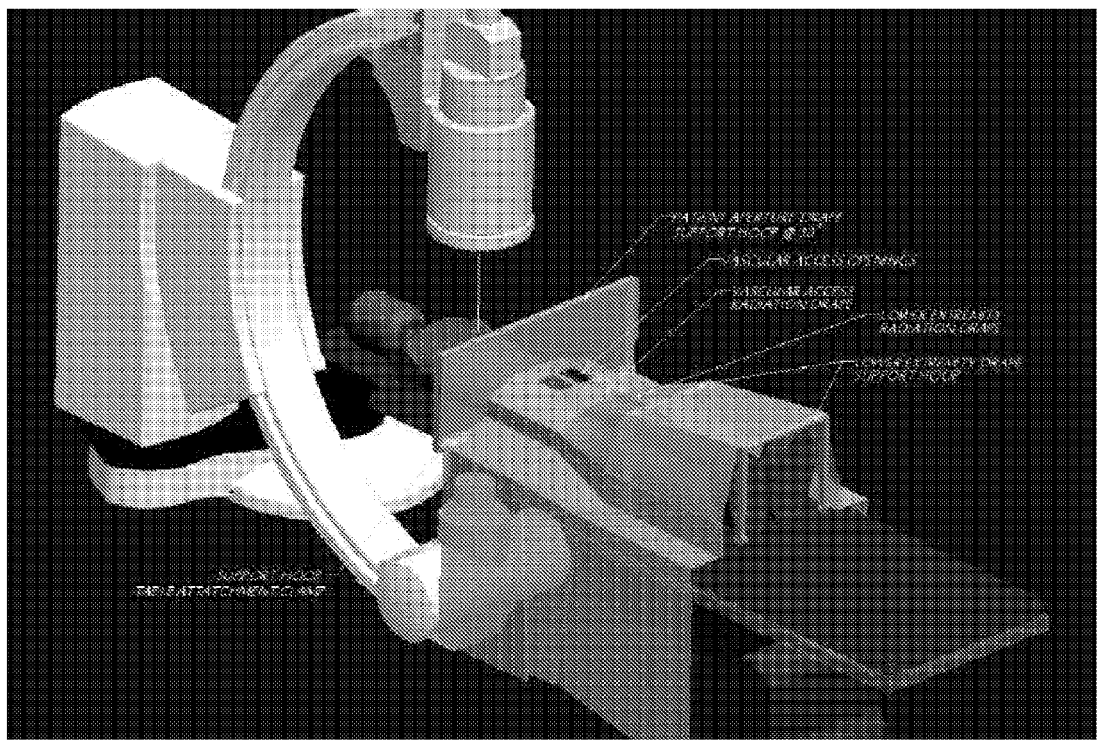
FIG. 5 is a perspective of an embodiment according to principles of the present invention in relation to the C-arm and radiation source, but with the radiation-shielding barrier removed.

Referring to FIG. 5, an embodiment of the present invention is shown, with the radiation-shielding barrier 22 removed for clarity. The location of the radiation source 36 and C-arm is shown with respect to the opening in the radiation barrier, the table 34, the patient, and the interface 70. As shown in FIG. 5, the barrier 22 remains between medical personnel and the radiation source 36 at all times during a radiologic procedure. The interface 70 protects medical personnel from radiation that may escape through the opening in the barrier 22. The radiation-resistive drape 72 protects medical personnel from radiation that may escape through the patient, especially the lower extremities.

Figure 6:
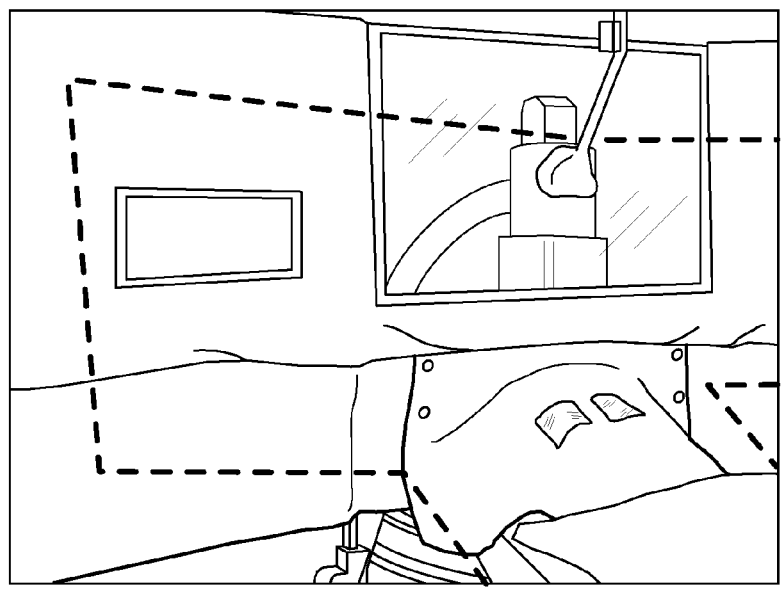
FIG. 6 is a perspective of an embodiment according to principles of the present invention in relation with the dotted line indicating the outline of the sterile draping when attached to the radiation-shielding barrier.

Referring to FIG. 6, a perspective of an embodiment of the present invention is shown. In FIG. 6, the dotted line indicates the outline of a sterile drape that attaches to the radiation-shielding barrier. The sterile drape covers the interface and a portion of the radiation-resistive drape. In some preferred embodiments, the sterile drape is disposable. By using disposable sterile drapes medical personnel can maintain a sterile environment while using the interface and radiation-resistive drape, repeatedly.

In some embodiments, the present invention includes methods for shielding medical personnel from radiation emitted by a radiation source during a radiologic procedure performed on a patient. The patient is supported by a table. A radiation-shielding barrier is positioned between the medical personnel and the radiation source. The radiation-shielding barrier is also positioned adjacent the table. The radiation-shielding barrier includes an opening such that a portion of the table and the patient extends through the opening. A portion of the patient is covered with a first flexible sterile drape. A portion of the first flexible sterile drape is covered with a flexible radiation-resistive drape. At least a portion of the flexible radiation-resistive drape is covered with a second flexible sterile drape.

Figure 7:
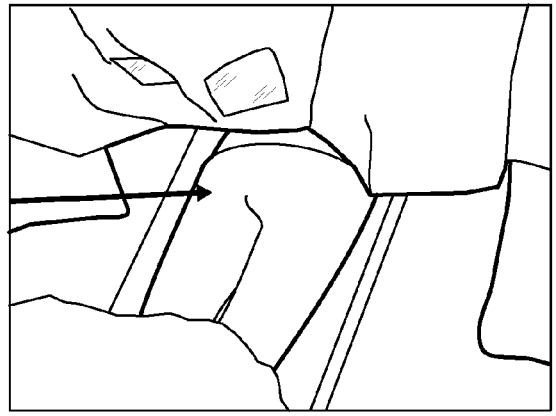
FIG. 7 is a perspective of an embodiment according to principles of the present invention in relation where the patient is covered with a sterile drape.

Referring to FIG. 7, an embodiment of the present invention is shown. A portion of the patient is covered with a first flexible sterile drape. The first sterile drape shown in FIG. 7 includes two vascular access apertures. One of the vascular access apertures is covered by a sterile, disposable cover adhesively attached to the first drape. FIG. 7 also shows the underside of the interface and the radiation-resistive drape.

Figure 8:
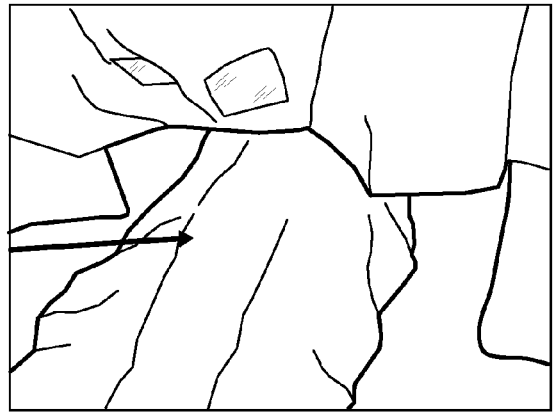
FIG. 8 shows a perspective of an embodiment according to principles of the present invention where the sterile drape is covered with a radiation-resistive drape.

Referring to FIG. 8, an embodiment of the present invention is shown. A portion of the patient and the first drape shown in FIG. 7 is covered with the radiation-resistive drape. The radiation-resistive drape shown in FIG. 8 includes two vascular access apertures. The vascular access apertures of the first drape are substantially aligned with the vascular access apertures of the radiation-resistive drape. One of the vascular access apertures of the radiation-resistive drape is covered by a cover adhesively attached to the radiation-resistive drape. In some preferred embodiments, the covers are sterile and disposable. FIG. 8 also shows the underside of the interface and a second flexible sterile drape.

Figure 9:
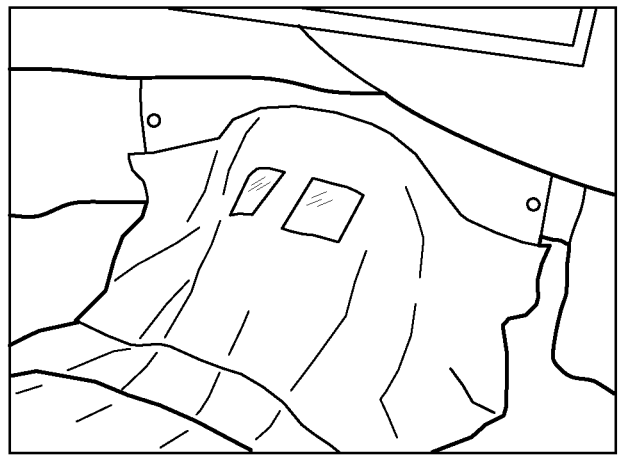
FIG. 9 shows a perspective of an embodiment according to principles of the present invention where the radiation-resistive drape is covered with a patient aperture drape.

Referring to FIG. 9, an embodiment of the present invention is shown. A portion of the patient is covered with the interface. The interface attaches to the barrier and covers the opening in the barrier and also a portion of the patient. The interface shown in FIG. 7 includes two vascular access apertures. The vascular access apertures of the interface are substantially aligned with the vascular access apertures of the radiation-resistive drape and the first drape.

Figure 10:
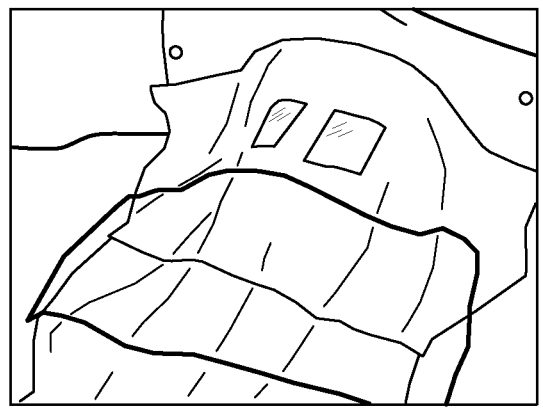
FIGS. 10 and 11 show perspectives of an embodiment according to principles of the present invention where the patient aperture drape is covered with a sterile drape.
Figure 11:
Figure 12A:
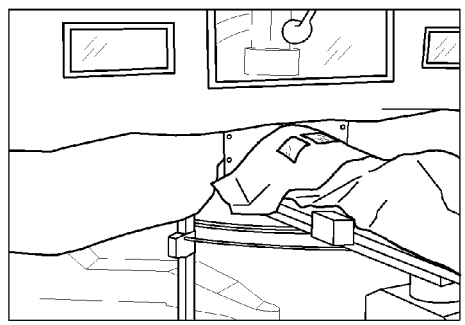
FIGS. 12a-d show perspective views of an embodiment according to principles of the present invention.
Figure 12B:
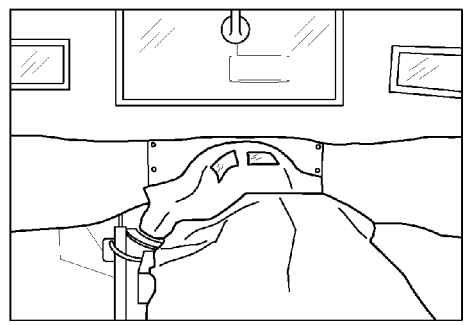
Figure 12C:
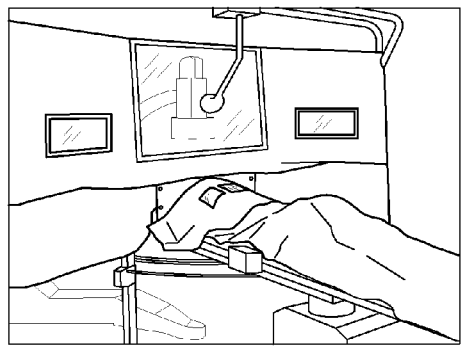
Figure 12D:
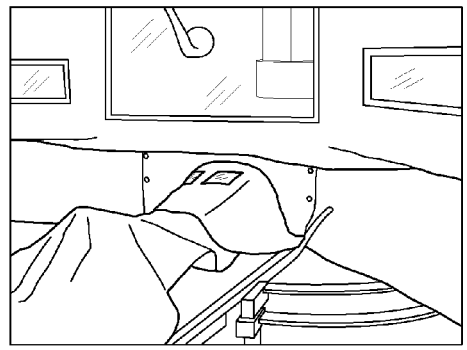

Referring to FIGS. 10 and 11, an embodiment of the present invention is shown. A portion of the patient is covered with a second flexible sterile drape. The second drape shown in FIGS. 10 and 11 include two vascular access apertures. In FIG. 10, the second drape covers a portion of the interface and the radiation-resistive drape, but not the vascular access apertures. In FIG. 11, the second drape covers a portion of the interface and the radiation-resistive drape, including the vascular access apertures. In FIG. 11, the vascular access apertures of the second drape are substantially aligned with the vascular access apertures of the interface, the radiation-resistive drape and the first drape. One of the vascular access apertures is covered by a sterile, disposable cover adhesively attached to the second drape.

Referring to FIGS. 12a, 12b, 12c and 12d, four different perspectives of an embodiment of the present invention is shown. The second sterile drape shown if FIG. 12 covers a portion of the interface and the radiation-resistive drape. The second drape attaches to the barrier.

Figure 13A:
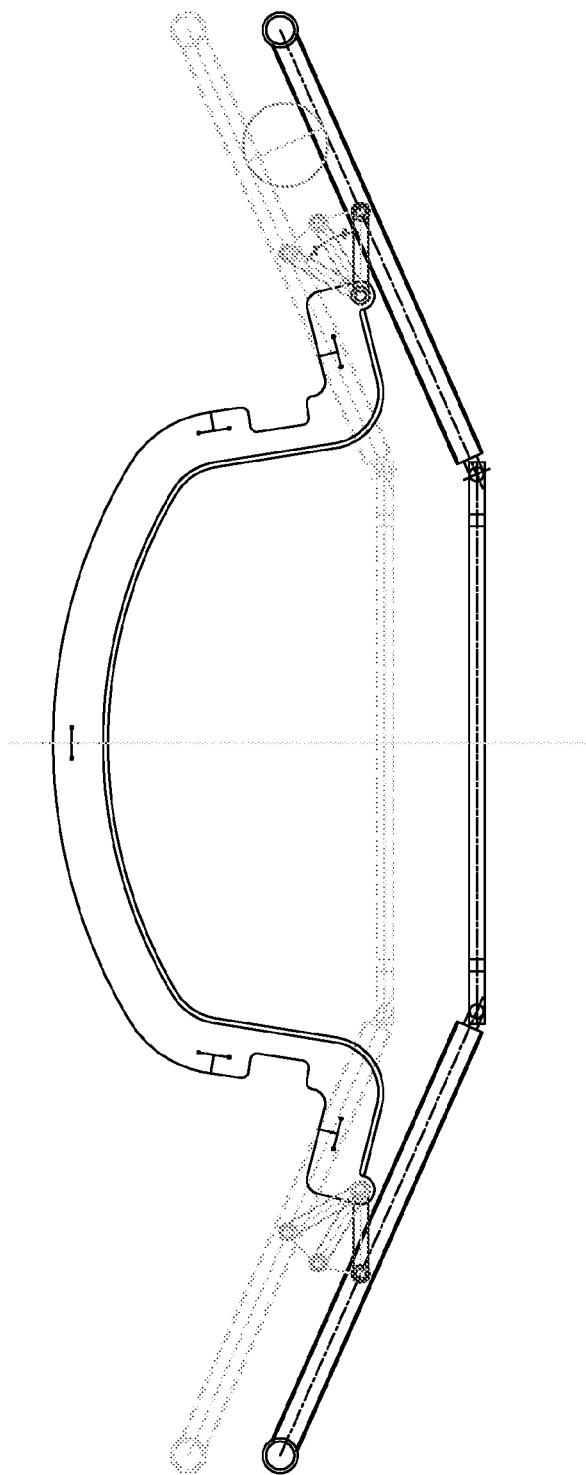
FIGS. 13a-b illustrate a presently preferred embodiment of apparatus for connecting a lower shield to an upper shield according to principles of the present invention.
Figure 13B:
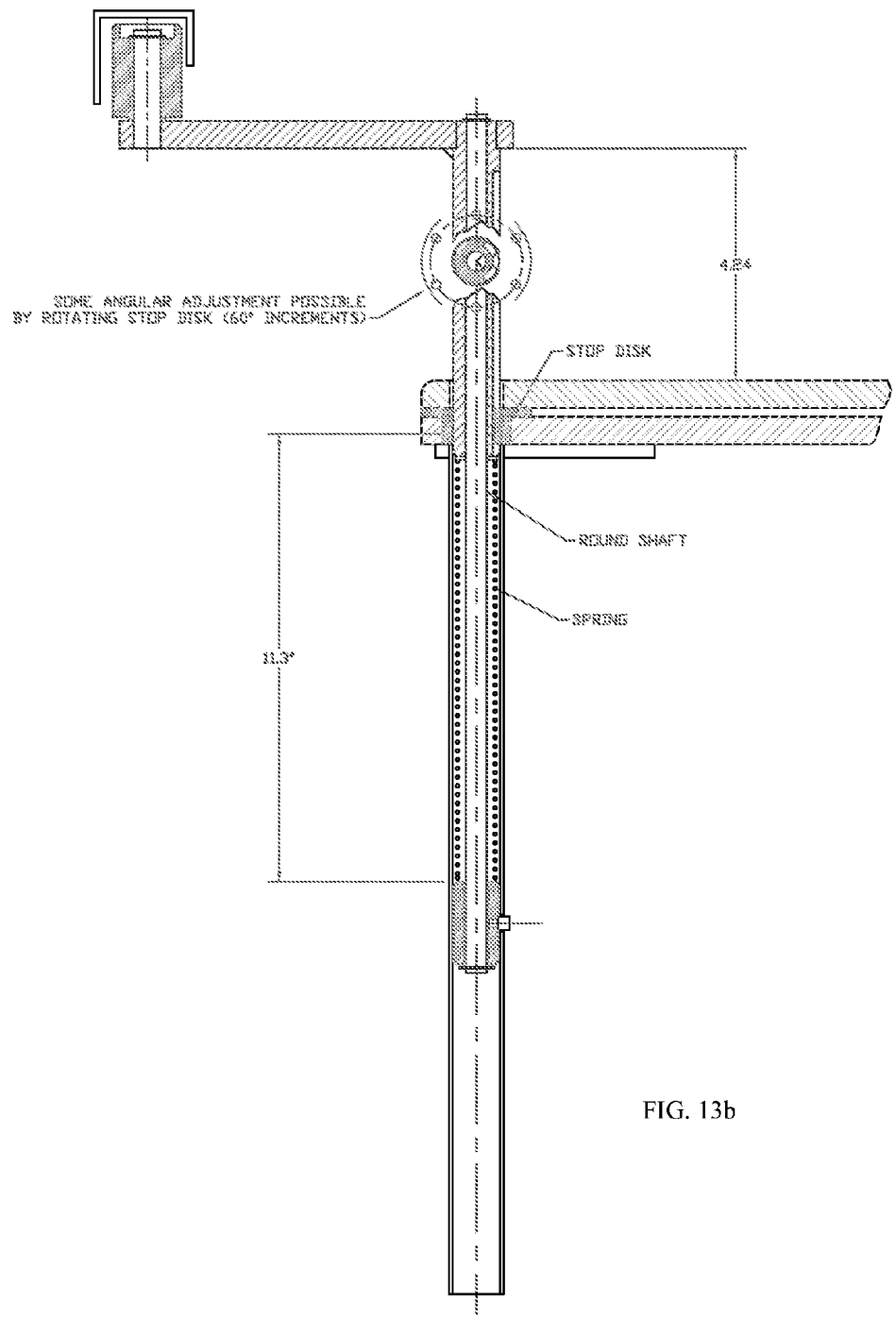
Figure 14A:
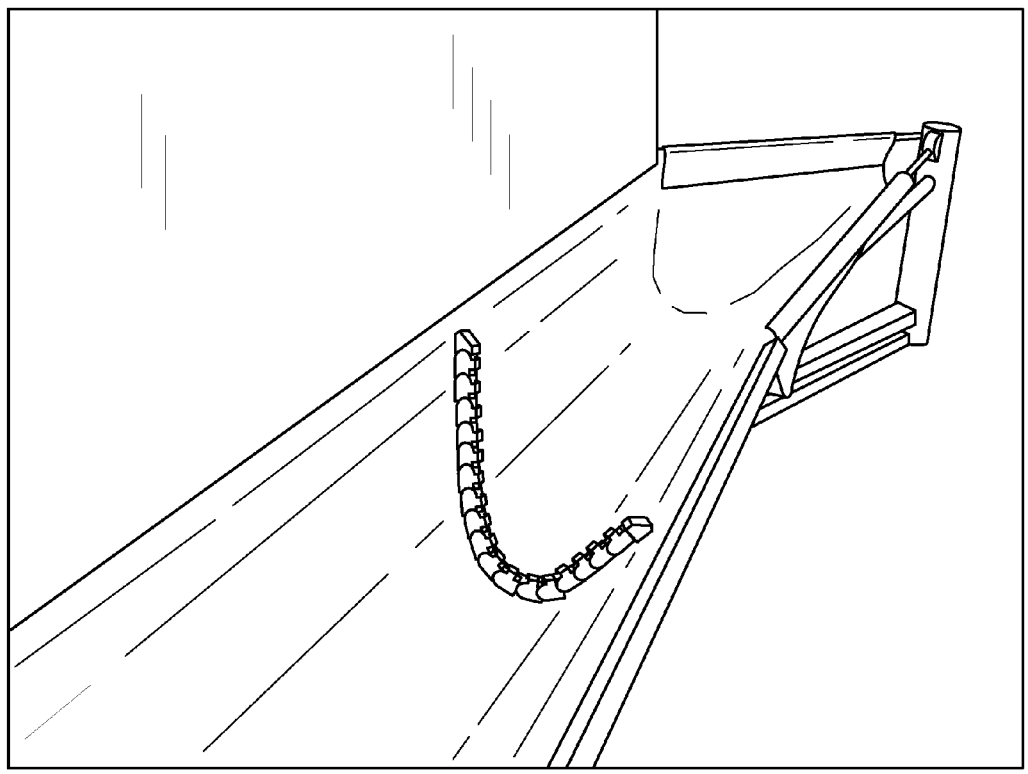
FIGS. 14a-14e illustrate an interconnect drape mechanism which maintains the radiation barrier at all times during a procedure according to principles of the present invention.
Figure 14B:
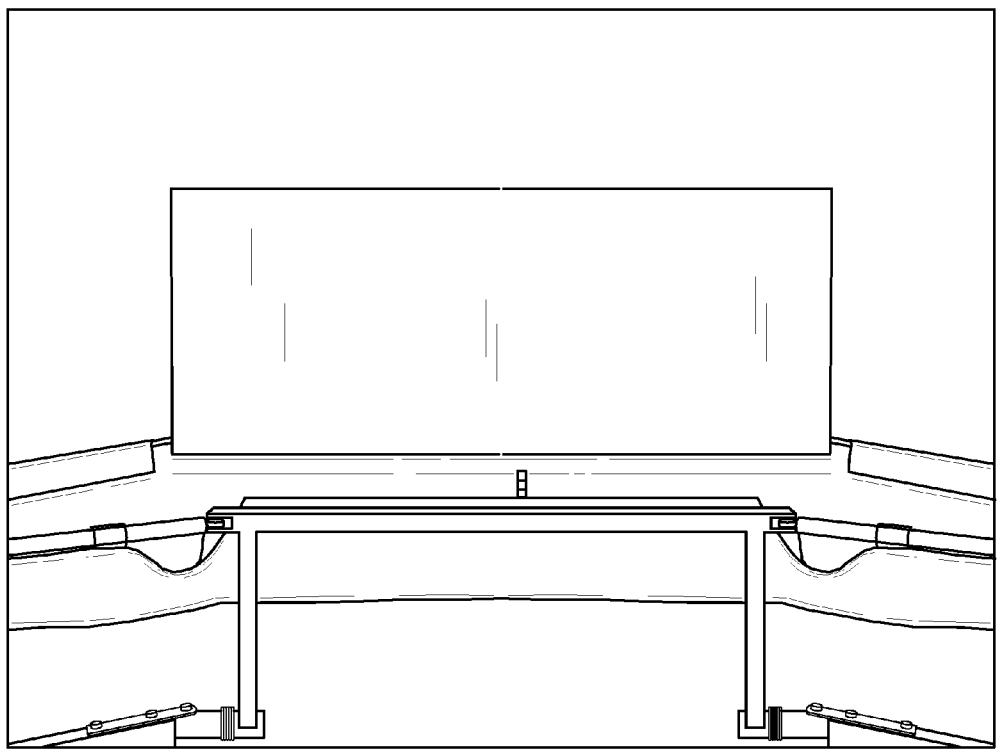
Figure 14C:
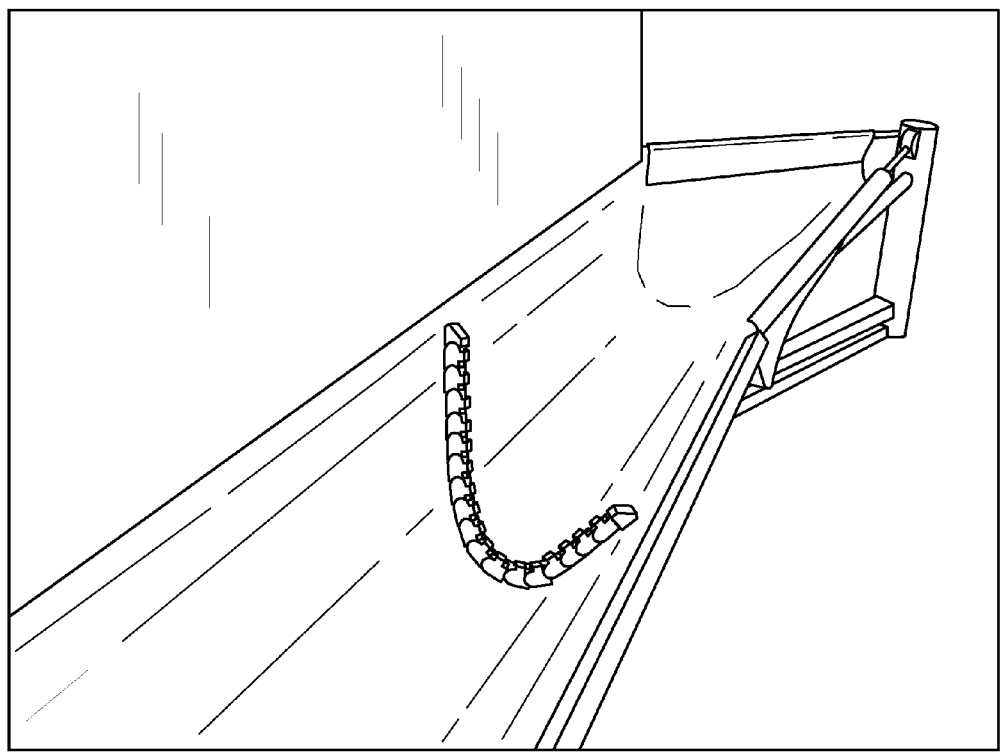
Figure 14D:
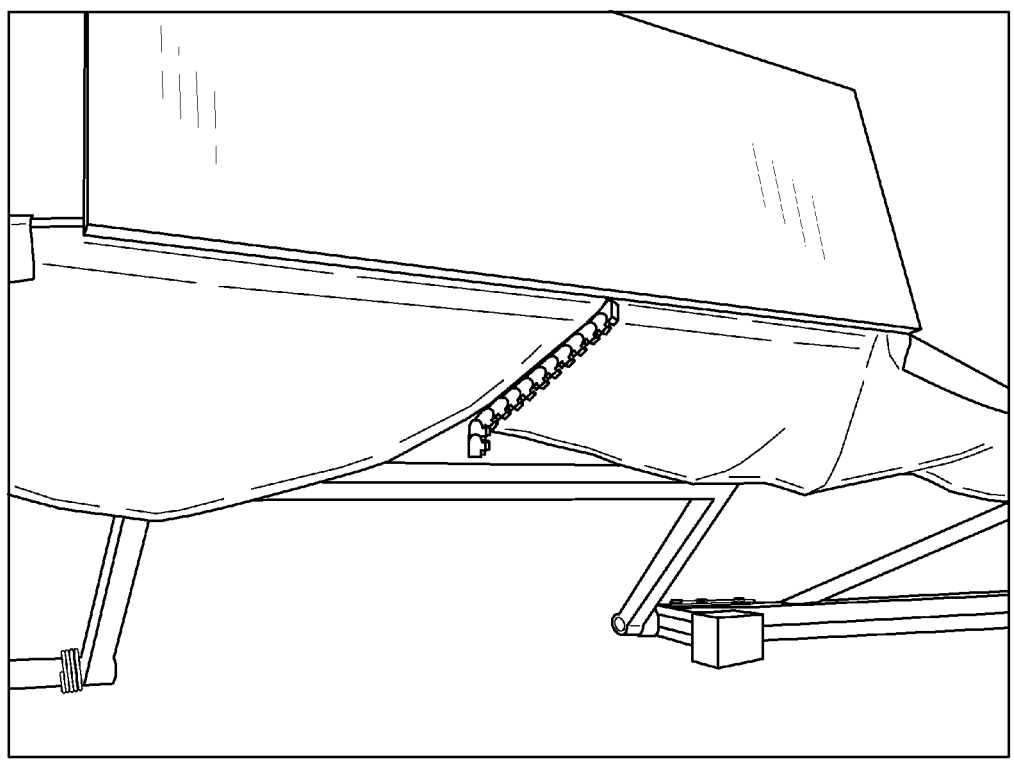
Figure 14E:
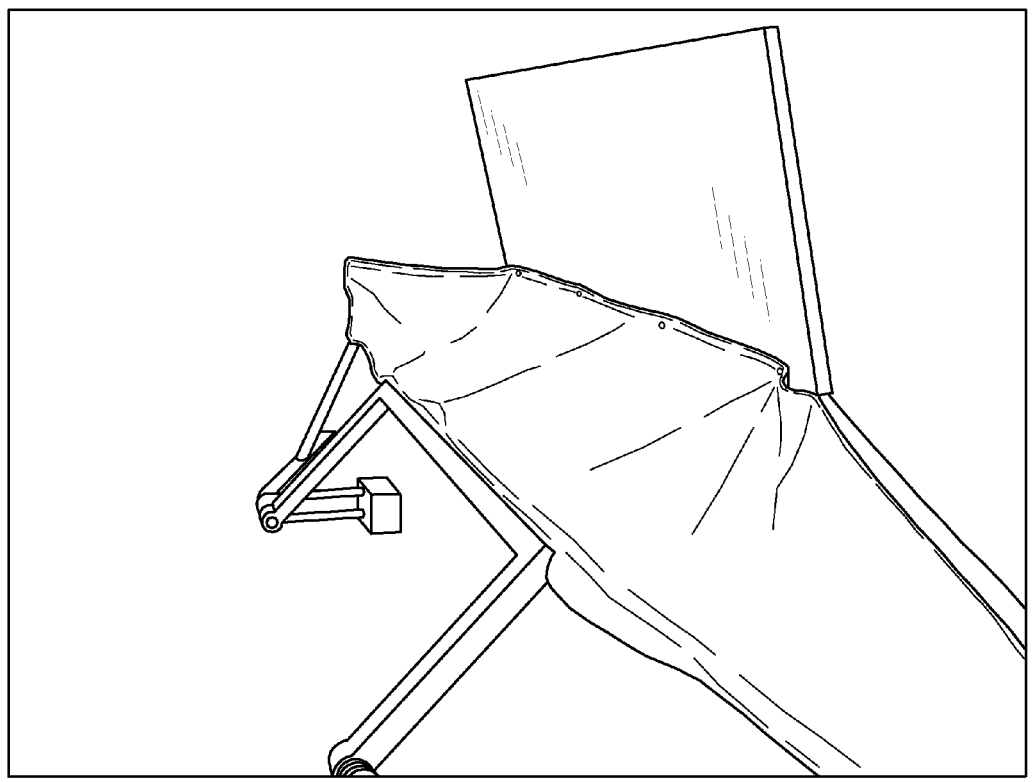

FIGS. 13 a-b disclose a linking mechanism of a preferred embodiment of the present invention wherein the lower shield is movably attached to the upper shield. An arm (e.g., a 3 inch metal or plastic member) is attached at one end to a top portion of a post of the lower shield and is movably attached via a hinged attachment or bearing at the other end of the arm to allow movement via a track attached to the upper shield. The use of the bearing facilitates a sufficient amount of movement (e.g., a 6 inch circular motion) without the need to move the lower shield. The angular movement of the linking mechanism is limited to a predetermined range which limits the relative positioning of the lower shield to the upper shield. In a preferred embodiment the range of free motion include a 6 inch diameter zone (shown in FIG. 13a) and lateral movement is relatively more limited such that the actual range of independent motion is an elongated ellipse that encloses a 6 inch diameter. The linking mechanism in configured such that the lower shield travels over the channel and deflects or moves the skirt of shielding at a bottom portion of the lower shield, which ensures there are no gaps or penetration to the radiation barrier.

During a panning movement, for example, this novel mechanism allows for the operator to move the table and the upper shield, while the lower shield remains fixed, and allows for the radiation barrier to be properly maintained.

FIGS. 14a-14e illustrate a preferred embodiment of the present invention wherein the interconnect drape is provided with a mechanism to ensure the radiation barrier is maintained during operation. As illustrated in the drawings, a unidirectional chain (e.g. a plastic e-chain) is provided at predetermined locations along on an underneath portion of the interconnect drape. In operation, when the patient hoop and/or window are moved toward a vertical configuration (that is, straight up and down) the chain allows the interconnect drape to lower on the patient side of the window, maintaining the radiation barrier at all times during the procedure. Although the preferred embodiment has been described by reference to the use of a unidirectional chain, it is foreseen that other mechanisms could be utilized as well, for example, bolts and metal stays. These mechanisms have been described in reference to the interconnect drape, but it is also foreseen that the mechanisms could also be utilized anywhere in the present invention as appropriate to maintain the radiation barrier in the case of movement of two or more portions of the system.

Figure 15A:
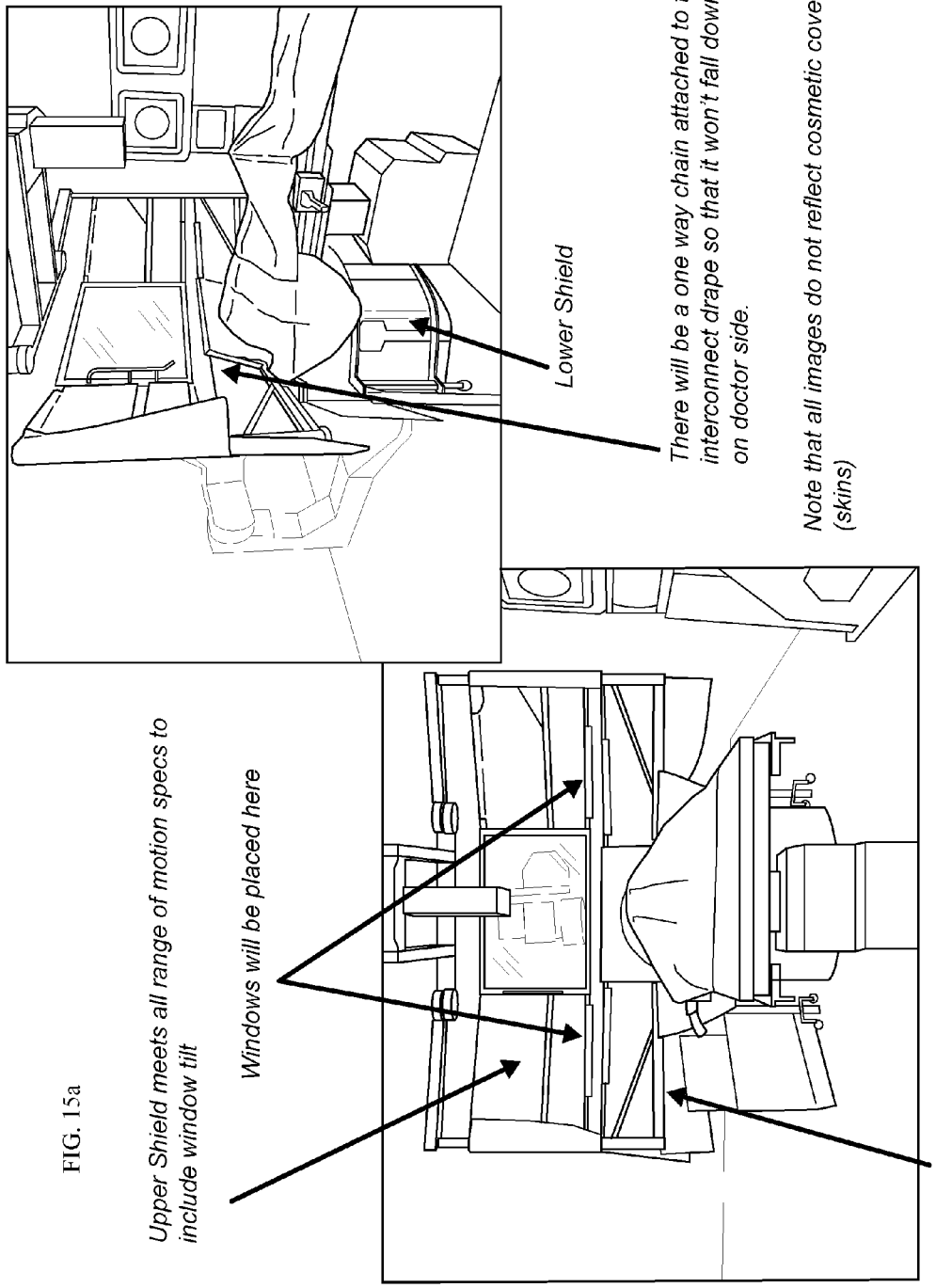
FIGS. 15a-d illustrate additional embodiments according to principles of the present invention.

FIGS. 15a-d illustrate a preferred embodiment of the present invention. As shown in FIG. 15a, the upper shield includes several radiopaque panels (II). These panels are interchangeable with radiopaque transparent windows. The upper shield is arranged so as to accommodate for a wide variety of positions and range of motion of the radiation source and C-arm with respect to the table (I). The location of the track that connects the upper shield to the lower shield is also shown (III).

Figure 15B:
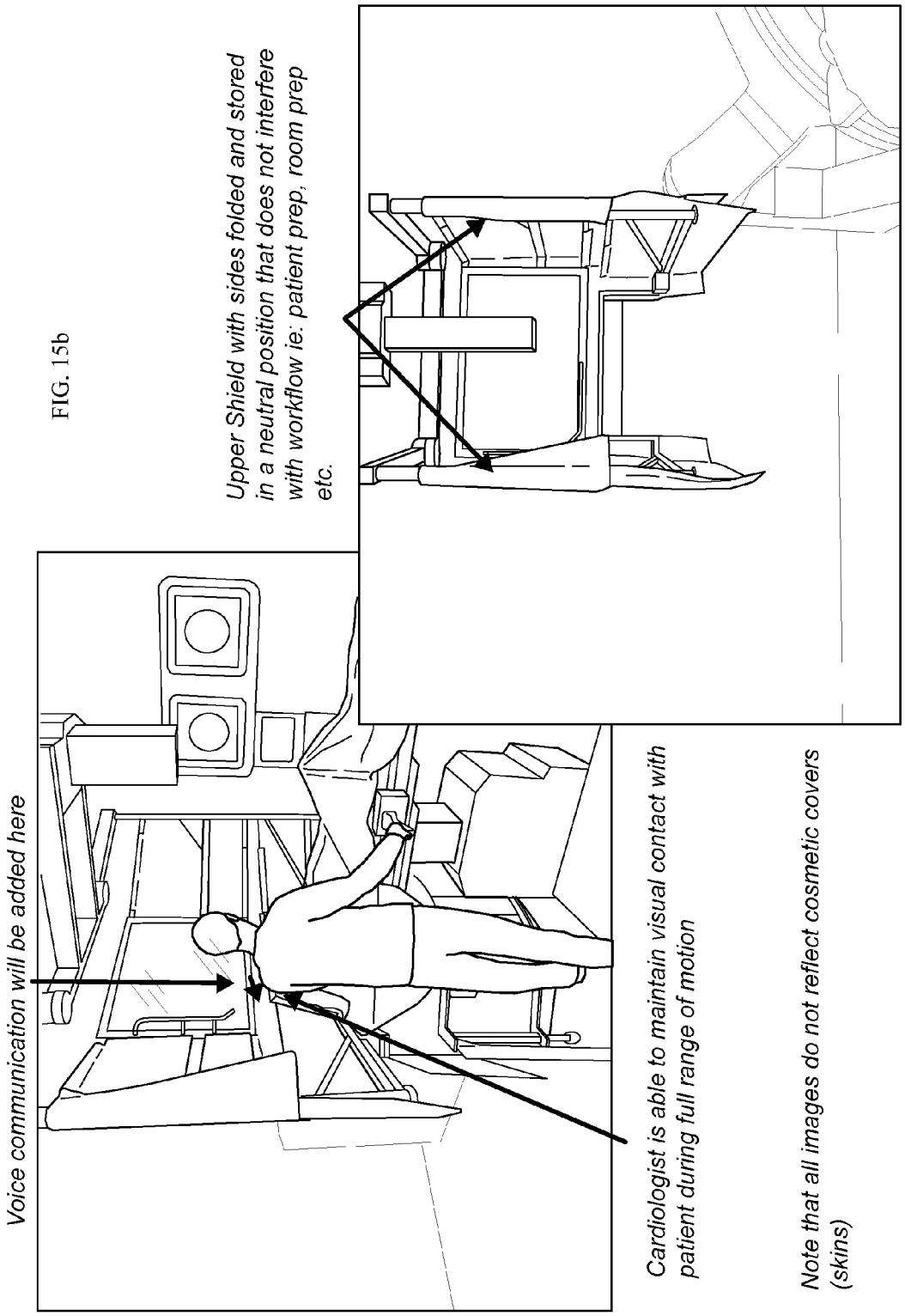

As shown in FIG. 15b, the lower shield is more clearly visible with respect to the table and the upper shield (II). A unilateral chain attaches to the interconnect drape such that the drape is prevented from falling down on the doctor side of the radiation barrier (I).

Figure 15C:
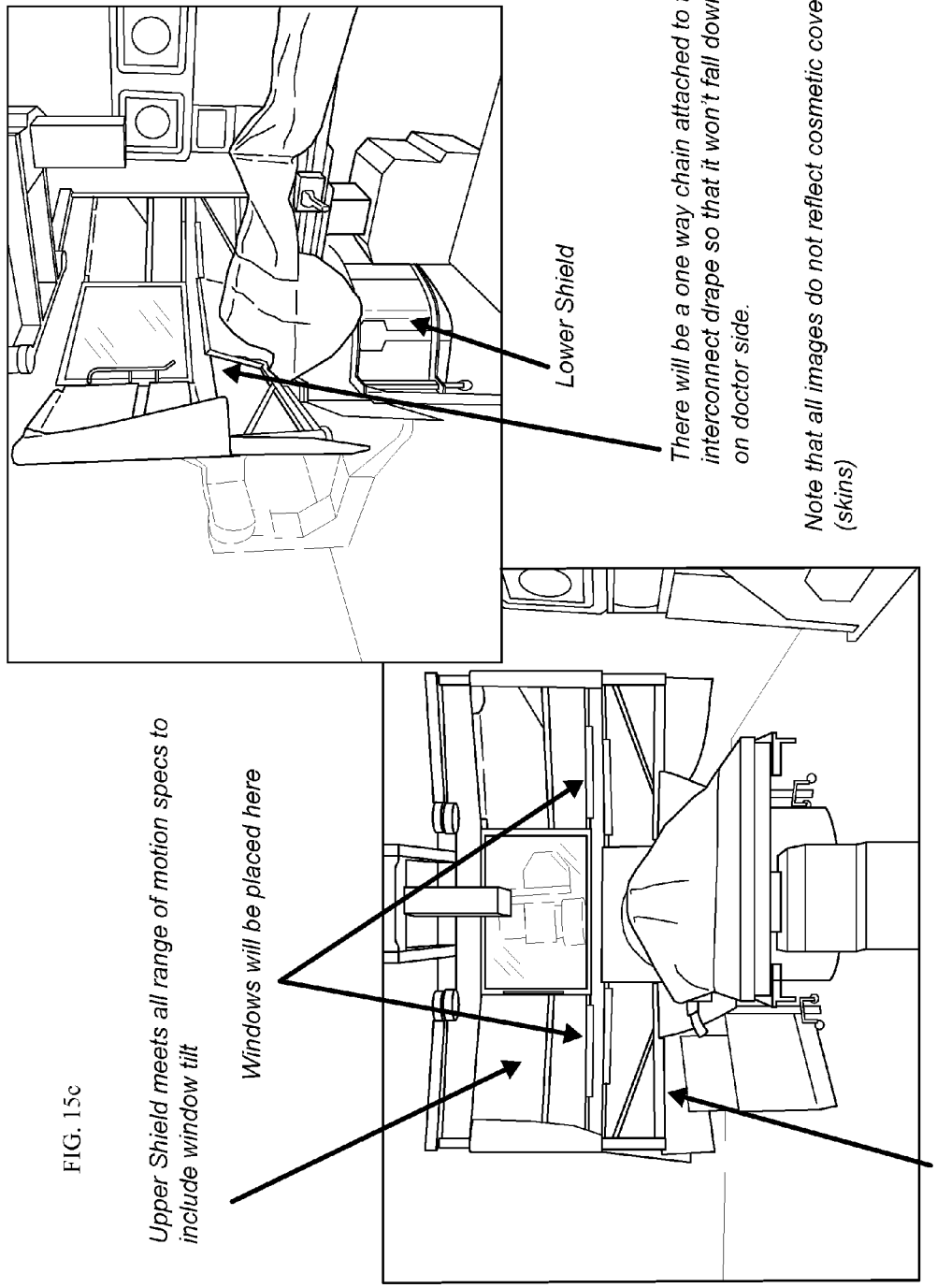

As shown in FIG. 15c, the position of medical personnel with respect to the patient is shown. In some embodiments, a module for voice communication is included along the radiation barrier in close proximity to the anticipated location of the head of the medical personnel (I). In this arrangement, the medical personnel are able to maintain visual contact with the patient through a radiopaque, transparent window, during the full range of motion of the system, without breaking the radiation barrier (II).

Figure 15D:
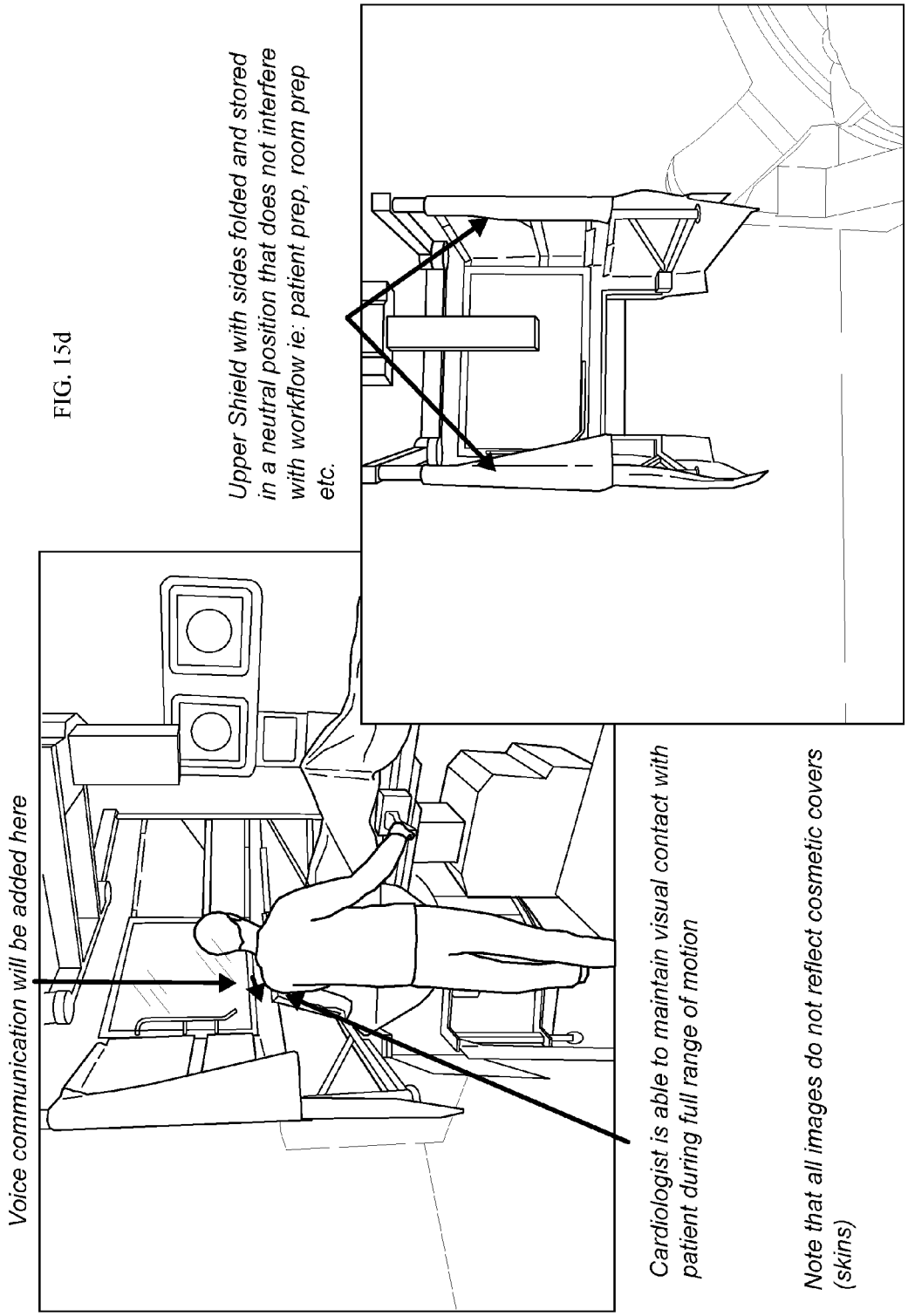

As shown in FIG. 15d, the upper shield is shown with sides folded and stored in a neutral position that does not interfere with workflow (i.e., patient prep, room prep, etc) (I).

The present invention also comprises encapsulating lead barriers in sterile environments. For example, a conventional lead barrier may be encapsulated in a sterile vinyl covering in a variety of shapes and sizes as appropriate to provide a sterile radiation barrier.

In the foregoing description, certain terms have been used for brevity, clearness and understanding; but no unnecessary limitations are to be implied therefrom beyond the requirements of the prior art, because such terms are used for descriptive purposes and are intended to be broadly construed. Moreover, the description and illustration of the inventions is by way of example, and the scope of the inventions is not limited to the exact details shown or described.

Although the foregoing detailed description of the present invention has been described by reference to an exemplary embodiment, and the best mode contemplated for carrying out the present invention has been shown and described, it will be understood that certain changes, modification or variations may be made in embodying the above invention, and in the construction thereof, other than those specifically set forth herein, may be achieved by those skilled in the art without departing from the spirit and scope of the invention, and that such changes, modification or variations are to be considered as being within the overall scope of the present invention. Therefore, it is contemplated to cover the present invention and any and all changes, modifications, variations, or equivalents that fall with in the true spirit and scope of the underlying principles disclosed and claimed herein. Consequently, the scope of the present invention is intended to be limited only by the attached claims, all matter contained in the above description and shown in the accompanying drawings shall be interpreted as illustrative and not in a limiting sense.

Having now described the features, discoveries and principles of the invention, the manner in which the invention is constructed and used, the characteristics of the construction, and advantageous, new and useful results obtained; the new and useful structures, devices, elements, arrangements, parts and combinations, are set forth in the appended claims.

It is also to be understood that the following claims are intended to cover all of the generic and specific features of the invention herein described, and all statements of the scope of the invention which, as a matter of language, might be said to fall therebetween.

What is claimed is:

1. A method for shielding medical personnel from radiation emitted by a radiation source during a radiologic procedure performed on a patient supported by a table, comprising:

positioning a radiation-shielding barrier between the medical personnel and the radiation source, and adjacent the table such that a portion of the table extends through an opening in the radiation-shielding barrier;

covering at least a portion of the patient with a first flexible sterile drape; covering the opening in the radiation-shielding barrier and at least a portion of the first flexible sterile drape with a flexible radiation-resistive drape; and covering at least a portion of the flexible radiation-resistive drape with a second flexible sterile drape.

2. The method of claim 1, wherein the first and second flexible sterile drapes are disposable.

3. The method of claim 1, wherein the flexible radiation-resistive drape is reusable.

4. The method of claim 1, wherein the first and second flexible sterile drapes are connected.

5. The method of claim 1, wherein the first and second flexible sterile drapes are connected such that a pocket is formed between the first and second flexible sterile drapes.

6. The method of claim 5, wherein the flexible radiation-resistive drape is inserted in the pocket formed between the first and second flexible sterile drapes.

7. The method of claim 1, wherein the first and second flexible sterile drapes comprise a single sheet folded over on top of itself.

8. The method of claim 1, further comprising: attaching at least one of the first and second flexible sterile drapes and the flexible radiation-resistive drape to the radiation-shielding barrier.

9. The method of claim 8, wherein said attaching at least one of the first and second flexible drapes and the flexible radiation-resistive drape to the radiation barrier uses a fastener selected from a group of fasteners consisting of a hook and loop fastener, a Velcro fastener, a screw fastener, a snap fastener, and an adhesive.

10. The method of claim 1, wherein the first and second flexible sterile drape and the flexible radiation-resistive drape generally extend between at least a lower portion to a middle portion of the patient.

11. The method of claim 1, wherein the radiation barrier comprises a patient aperture hoop of adjustable size, through which a portion of the table extends.

12. A system for shielding medical personnel from radiation emitted by a radiation source during a radiologic procedure performed on a patient, comprising:

a table for supporting a patient during a radiologic procedure;

an upper shield adjacent and above the table such that a portion of the table extends through an opening in the upper shield; a lower shield extending below the table;

a linking mechanism between the upper and lower shield; wherein the lower shield and the upper shield overlap such that radiation does not leak between the two; and the linking mechanism attaches the upper shield to the lower shield such that both the upper shield and lower shield can be moved independent of one another within a range of motion without opening a gap between the two through which radiation can leak.

13. The system of claim 12, wherein the linking mechanism comprises: an arm attached at one end to a top portion of a post of the lower shield and is moveably attached via a bearing at the other end of the arm to a track along the bottom of the upper shield.

14. The system of claim 12, further comprising: a flexible radiation-resistive interconnect drape to at least partially cover the opening in the upper shield; and at least one unidirectional chain arranged along the underside of the interconnect drape arranged such that when the upper shield is moved with respect to the table, the interconnect drape maintains the radiation barrier, and the unidirectional chain is flexible when the chain is extended in a first direction and supportive when extended in a second direction.

15. The system of claim 12, further comprising: a first flexible sterile drape covering at least a portion of the patient; a flexible radiation-resistive drape covering the opening in the upper shield and at least a portion of the first flexible sterile drape; and a second flexible sterile drape covering at least a portion of the flexible radiation-resistive drape.

\* \* \* \* \*